United States Patent [19]

Grollier et al.

[11] Patent Number: 5,032,382

[45] Date of Patent: Jul. 16, 1991

[54] LIGHT-STABLE SCREENING COSMETIC COMPOSITION CONTAINING BIXIN COMBINED WITH A LIPID-SOLUBLE UV FILTER AND ITS USE FOR PROTECTING THE HUMAN EPIDERMIS AGAINST ULTRA-VIOLET RADIATION

[75] Inventors: Jean F. Grollier, Paris; Jean Cotteret, Verneuil sur Seine; Georges Rosenbaum, Asnières, all of France

[73] Assignee: L'Oreal, Paris, France

[21] Appl. No.: 244,746

[22] Filed: Sep. 14, 1988

[30] Foreign Application Priority Data

Sep. 21, 1987 [LU] Luxembourg ............................ 86997

[51] Int. Cl.$^5$ .......................... A61K 7/42; A61K 7/44; A61K 9/10; A61K 9/12

[52] U.S. Cl. ................... 424/047; 424/DIG. 5; 424/059; 424/060; 424/195.1; 514/847; 514/873; 514/937; 514/938

[58] Field of Search .................. 424/47, 60, 195, 59

[56] References Cited

U.S. PATENT DOCUMENTS

| | | | |
|---|---|---|---|
| 2,418,695 | 3/1947 | Brown | 424/59 |
| 2,815,287 | 12/1957 | Barnett et al. | 560/191 |
| 2,890,225 | 6/1959 | Gregory | 424/59 X |
| 3,123,647 | 3/1964 | Duennenberger et al. | 424/59 |
| 4,668,505 | 5/1987 | Grollier et al. | 424/047 |

FOREIGN PATENT DOCUMENTS

| | | | |
|---|---|---|---|
| 1593929 | 12/1970 | Fed. Rep. of Germany | 424/59 |
| 2509989 | 7/1981 | France | 424/60 |
| 2555447 | 11/1983 | France | 424/59 |
| 2555447 | 5/1985 | France | 424/59 |
| 2589728 | 11/1985 | France | 424/59 |
| 2589728 | 11/1986 | France | 424/59 |

*Primary Examiner*—Dale R. Ore
*Attorney, Agent, or Firm*—Marshall, O'Toole, Gerstein, Murray & Bicknell

[57] ABSTRACT

The invention relates to a light-stable cosmetic composition for protecting the human epidermis against UV radiation, containing at least 0.0025% by weight of bixin combined with at least 1% by weight of one or more lipid-soluble agents screening UV radiation, chosen from 3-benzylidene-dl-camphor, its derivatives and benzophenone derivatives, in a cosmetically acceptable vehicle comprising at least one fatty phase.

The bixin takes the form of an oily extract of annatto containing at least 0.1% by weight of bixin.

17 Claims, No Drawings

LIGHT-STABLE SCREENING COSMETIC COMPOSITION CONTAINING BIXIN COMBINED WITH A LIPID-SOLUBLE UV FILTER AND ITS USE FOR PROTECTING THE HUMAN EPIDERMIS AGAINST ULTRA-VIOLET RADIATION

The present invention relates to a light-stable screening cosmetic composition containing bixin combined with at least one lipid-soluble UV filter chosen from benzylidene camphor and its derivatives and benzophenone derivatives, as well as to the use of such a composition for protecting the epidermis against ultraviolet radiation.

It is known that light radiation of wavelengths between 280 and 400 nm enable the human epidermis to tan, and that rays of wavelengths between 280 and 320 nm, known by the name of UV-B, cause erythema and skin burns.

It has already been proposed, according to French patent applications 2,555,447 and 2,589,728, to use substances extracted from annatto (*Bixa orellana*) seeds for protecting the skin from the harmful effects of UV-B solar radiation.

However, the oily extracts proposed, obtained by maceration of annatto seeds comminuted by grinding, in various oils, do not retain all the chemical activity of the active principle of the extract, namely bixin, which is responsible for the absorption of ultraviolet radiation in the erythemal UV-B region, as a result of a sensitivity to oxidation and a degradation due to atmospheric agents.

In addition, it has been found that extracts of annatto seeds have a relatively low screening power with respect to UV radiation.

While attempting to combine various agents screening UV radiation with lipid-soluble extracts of annatto seeds containing bixin, in order to improve their screening power with respect to UV, and in particular UV-B, radiation, the Applicants found, altogether surprisingly, that some lipid-soluble screening agents, chosen from 3-benzylidene-dl-camphor and its derivatives and benzophenone derivatives, enabled a photochemically and chemically stable screening composition to be obtained which possessed, in addition, an improved index of protection.

The index of protection (IP) of a screening composition is known to be defined as the following ratio:

$$IP = \frac{\text{Mininimal erythemal dose (MED) with screening composition}}{\text{Minimal erythemal dose (MED) without screening composition}},$$

the minimal erythemal dose being the energy (in mJ/cm$^2$) which has to be applied in order to see the appearance of a very slight erythema.

The subject of the present invention is hence a light-stable cosmetic composition for protecting the human epidermis against ultraviolet radiation, comprising at least 0.0025% by weight of bixin combined with at least by weight of lipid-soluble UV filter, chosen from 3-benzylidene-dl-camphor and its derivatives, benzophenone derivatives and their mixtures, in a cosmetically acceptable vehicle containing at least one fatty phase.

The subject of the invention is also a process for protecting the human epidermis against ultraviolet radiation, consisting in applying on the skin an effective quantity of a light-stable screening cosmetic composition as defined above.

In the screening cosmetic composition according to the invention, bixin possesses the advantageous property of reducing the solar erythema, and it also acts as an antioxidant.

Bixin also possesses the considerable advantage of being non-toxic, thereby enabling a screening cosmetic composition to be obtained which is completely safe with respect to the human epidermis.

Bixin is also known to be the main constituent of an orange-red pigment, annatto, giving a yellow colouration at low concentration and repelling insects. Such properties are advantageous for the purpose of its use in a cosmetic composition intended for the human epidermis.

According to a preferred embodiment of the invention, bixin is used in the form of an oily extract of annatto seeds. This oily extract may take the form of a solution (lipid-soluble extract) or a suspension in an oil.

The lipid-soluble extract may be obtained, by way of illustration and without implied limitation, in the following manner.

Since the pigment (annatto) is present in the pericarp of the annatto seed, the lipid-soluble extract of annatto may be prepared according to the following processes:

1) The seeds are immersed in an oil at a temperature not exceeding 70° C., and they are subjected to a mechanical abrasion to remove their pericarp, by a process known as "raspelling"; the oily slurry obtained is then heated under vacuum at a temperature not exceeding 130° C., and the insoluble products are removed by filtration to separate the lipid-soluble extract of annatto; this process is described in "Food Chemistry", 1980, 5, p. 48.

2) It is also possible to make the seeds swell in water, stir in a fatty oil maintained at a temperature of 100° to 175° C. and containing at least 20% of free fatty acid, and then separate the oily fraction containing the pigment as described in U.S. Pat. No. 2,815,287.

3) It is also possible to prepare a dry extract of the pigment by the methods known in the art, preferably, for example, by extraction with a solvent (25% of chloroform in ethanol) ("Indian J. Dairy Sci." 1983, 36, 2, p. 160), and then to redissolve the dry extract obtained in a vegetable oil.

The suspension of annatto in a vegetable oil may be prepared, for example, according to the following processes, described in "Food Chemistry", 1980, 5, p. 48–49:

1) After the "raspelling", the pericarp extract is centrifuged and the finest particles are mixed with an oil to give a suspension in the oil.

2) The pigment is extracted in a solvent such as acetone, and the extracts are washed with hexane or another solvent in which the pigment is insoluble to remove the impurities and the odours. A grinding is then performed in a vegetable oil, until a particle size of approximately 10 pm and a microcrystalline suspension in the oil are obtained.

3) An extraction is performed using mono- and di-glycerides, free fatty acids or propylene glycol.

In the cosmetic composition according to the invention, it is possible to use any oily extract of annatto in various oils such as, for example, soybean oil, pequia oil, sweet almond oil, coffee oil or sunflower oil, containing variable quantities of bixin, at least greater than 0.1% by weight.

Especially preferred oily extracts of annatto seeds are the oily soybean extracts assaying at approximately 0.12% by weight of bixin (lipid-soluble extract) or approximately 3.8% by weight of bixin (suspension in oil).

The sunscreening composition according to the invention advantageously has a weight content of bixin of between 0.0025% and 0.06% by weight, and preferably between 0.0025% and 0.009% by weight.

Among lipid-soluble 3-benzylidene-dl-camphor derivatives used in combination with bixin according to the present invention, the following derivatives may be mentioned by way of examples:
— 3-(4-methylbenzylidene)-dl-camphor (EUSOLEX 6300);
— 3-benzylidenecamphors substituted at the para position, having the following formula:

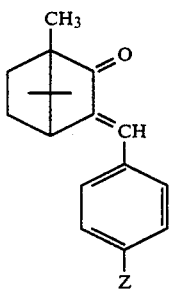
(I)

where Z denotes the groups —CH$_2$I, —CH$_2$Br or —CHBr$_2$, —CH$_2$R, —CHR'R', —CHO, —COOR" with:
R=—NR$_1$R$_2$, —OR$_4$, —OCOR$_5$, —SR$_6$, —CN, —COOR", (C$_1$-C$_4$ alkyl)sulphinyl,
R$_1$ and R$_2$=H, C$_1$-C$_{18}$ alkyl, C$_1$-C$_4$ hydroxyalkyl or alternatively form, together with the nitrogen atom, a heterocycle such as morpholine, piperidine or piperazine,
R$_4$=H, C$_1$-C$_{18}$ alkyl, C$_1$-C$_4$ hydroxyalkyl, polyoxyethylene, aryl such as phenyl or naphthyl, substituted or unsubstituted, menthyl, dialkylaminoalkyl in which the alkyl radicals contain from 1 to 4 carbon atoms,
R$_5$=C$_1$-C$_{18}$ alkyl, C$_2$-C$_{18}$ alkenyl, aryl such as phenyl or naphthyl, substituted or unsubstituted, 5- to 6-membered aromatic or non-aromatic heterocycle,
R$_6$=H, C$_1$-C$_4$ alkyl, C$_1$-C$_4$ aminoalkyl, C$_1$-C$_4$ hydroxyalkyl, aryl such as phenyl or naphthyl, substituted or unsubstituted, benzothiazolyl,
R'=—OR'$_4$ or —SR'$_6$, in which R'$_4$ and R'$_6$ can have, respectively, the same meanings as R$_4$ and R$_6$, except the meanings hydrogen, polyoxyethylene, hydroxyalkyl and aryl,
R"=C$_1$-C$_{18}$ alkyl or C$_2$-C$_{18}$ alkenyl;
these compounds are described in the Applicants French patents 2,383,904, 2,402,647 and 2,421,878;
the sulphonamides derived from 3-benzylidenecamphor described in the Applicants French patent no. 2,529,887, having the formula:

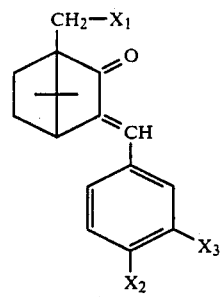
(II)

in which
X$_1$ denotes a hydrogen atom or a radical Y;
X$_2$ denotes a hydrogen or halogen atom, a C$_1$-C$_4$ alkyl or alkoxy radical or a radical Y or Z;
X$_3$ denotes a hydrogen or halogen atom, a C$_1$-C$_4$ alkyl or alkoxy radical or a radical Y or Z;
or alternatively X$_2$ and X$_3$ together form an alkylenedioxy group containing 1 or 2 carbon atoms;
Y denotes a radical

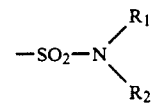

in which
R$_1$ denotes a hydrogen atom or a C$_1$-C$_4$ alkyl or hydroxyalkyl radical;
R$_2$ denotes a hydrogen atom, a linear or branched alkyl or alkenyl, cycloalkyl, aryl or aralkyl radical, these different radicals containing 1 to 20 carbon atoms and being capable of being substituted with one or more hydroxy, alkoxy or dialkylamino groups,
it not being possible for R$_1$ and R$_2$ simultaneously to denote a hydrogen atom;
Z denotes a group:
Z$_1$=

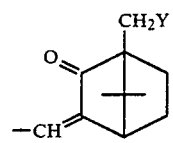

where Y has the meaning stated above
Z$_2$=

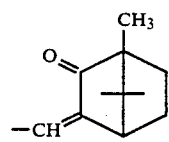

or
Z$_3$=

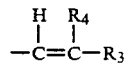

where $R_3$ denotes a hydrogen atom, a —CN radical or a radical —COR$_5$;

$R_4$ denotes a radical —COR$_6$, $R_5$ and $R_6$, which may be identical or different, denote $C_1$-$C_{20}$ alkoxy or alkylamino groups;

with the proviso that one of the symbols $X_1$, $X_2$ and $X_3$ is different from the other two, and that a) where $X_1$ denotes a hydrogen atom, $X_2$ and $X_3$ are different from one another and cannot assume the meanings $Z_2$ and $Z_3$, one of the two of necessity having the meaning Y or $Z_1$;

b) where $X_1$ has the meaning Y $X_2$ and $X_3$ are different from Y and cannot simultaneously assume the meaning $Z_1$ or $Z_2$ or $Z_3$.

The more especially preferred compounds of formula (II) are the following:

[Chemical structure: benzylidene camphor with SO$_2$NH—CH$_2$—CH(C$_2$H$_5$)—(CH$_2$)$_3$CH$_3$ substituent]

[Chemical structure: benzylidene camphor with SO$_2$CH$_2$—NH—CH$_2$—CH(C$_2$H$_5$)—(CH$_2$)$_3$CH$_3$]

and

[Chemical structure: benzylidene camphor with SO$_2$CH$_2$—NH—CH$_2$—CH(C$_2$H$_5$)—(CH$_2$)$_3$CH$_3$ and OC$_4$H$_9$, OCH$_3$ substituents]

It is preferable, however, according to the invention, to use 3-benzylidene-dl-camphor.

Among benzophenone derivatives which can be used according to the invention, the following may be mentioned:

—2-hydroxy-4-methoxybenzophenone (Uvinul M40),
—2-hydroxy-4-(n-octyloxy)benzophenone (Cyasorb UV 531 or Uvinul 408),
—4-phenylbenzophenone (Eusolex 3490),
—2-ethylhexyl 2-(4-phenylbenzoyl)benzoate (Eusolex 3573),
—2-hydroxy-4-methoxy-4'-methylbenzophenone (Uvistat 2211),
—2,2'-dihydroxy-4,4'-dimethoxybenzophenone (Uvinul D 49),
—2,2',4,4'-tetrahydroxybenzophenone (Uvinul D 50),
—2,4-dihydroxybenzophenone (Uvinul 400),
—2,2'-dihydroxy-4-methoxybenzophenone (Cyasorb UV 24).

Among the above compounds, it is preferable to use 2-hydroxy-4-methoxybenzophenone (Uvinul M40).

The screening agents mentioned above, namely 3-benzylidene-dl-camphor, its derivatives and benzophenone derivatives, are present in the screening cosmetic composition according to the invention in total proportions of between 1 and 20% by weight, relative to the total weight of the composition, and preferably between 2 and 10% by weight.

The screening cosmetic composition according to the invention can optionally contain other UV filters, such as water-soluble or lipid-soluble UV-A and UV-B filters which are well known in the prior art and compatible with bixin and the above UV filters.

On account of the lipid-soluble nature of the extract of annatto seeds and of the screening agents derived from benzylidenecamphor used in the cosmetic composition of the invention, the latter contains at least one fatty phase. It can take the form of an oily or oleoalcoholic lotion, the form of a fatty or oleoalcoholic gel or a solid stick, or alternatively the form of an emulsion such as a cream or milk; it can also be packaged as an aerosol and take the form of a foam.

As a solubilizing solvent, an oil or wax, or a lower polyol or monohydric alcohol, or mixtures thereof, may be used. The especially preferred monohydric alcohols or polyols are ethanol, isopropanol, propylene glycol, glycerin and sorbitol.

The screening cosmetic composition according to the invention can contain customary cosmetic adjuvants such as thickeners, emollients, moisturizing products, surfactants, preservatives, antifoams, oils, waxes, lanolin, perfumes, propellants, colourings, vitamins, opacifiers or any other ingredient customarily used in cosmetics.

One embodiment of the invention is an emulsion in the form of a cream or milk comprising, in addition to bixin and the lipid-soluble screening agent, fatty alcohols, fatty acid esters and, in particular, fatty acid triglycerides, fatty acids, lanolin, natural or synthetic waxes or oils, and emulsifiers, in the presence of water.

Another embodiment consists of an oily lotion based on fatty acid esters, natural or synthetic waxes and/or oils, or an oleoalcoholic lotion based on oils or waxes, fatty acid esters such as fatty acid triglycerides, and lower alcohols such as ethanol or glycols such as propylene glycol, or lower polyols such as glycerin or sorbitol.

The fatty gels comprise an oil or a wax and a thickener such as silica; the oleoalcoholic gels comprise, in addition, one or more lower polyols or alcohols, such as ethanol, propylene glycol or glycerin.

The solid sticks consist of fats such as natural or synthetic oils and waxes, fatty alcohols, fatty acid esters and lanolin.

In the case of a composition packaged as an aerosol, traditional propellants, such as alkanes, fluoroalkanes and chlorofluoroalkanes, are used.

The examples which follow are designed to illustrate the invention, no limitation of the latter being implied.

EXAMPLE 1

A sun cream having the following composition is prepared:

| | |
|---|---|
| Mixture of 80% cetyl/stearyl alcohol and 20% cetyl/stearyl alcohol oxyethylenated with 33 mol of ethyleneoxide | 7 g |
| Mixture of non-self-emulsifying glycerol mono- and distearates | 2 g |
| Cetyl alcohol | 1.5 g |
| Liquid paraffin | 15 g |
| 2-Hydroxy-4-methoxybenzophenone (UVINUL M 40) | 1 g |
| 3-Benzylidene-dl-camphor | 1.5 g |
| Extract of annatto in soybean oil, assaying at approximately 3.8% of bixin (suspension | 0.1 g |

-continued

| | |
|---|---|
| in oil) | |
| Glycerin | 20 g |
| Perfume, colouring, preservative qs | |
| Water qs | 100 g |

EXAMPLE 2

A sun oil having the following composition is prepared:

| | |
|---|---|
| 3-Benzylidene-dl-camphor | 2.5 g |
| Sweet almond oil | 3 g |
| Extract of annatto in soybean oil, assaying at approximately 0.12% of bixin (lipid-soluble extract) | 5 g |
| Perfume, preservative, colouring qs | |
| Rapeseed oil qs | 100 g |

EXAMPLE 3

A sun cream having the following composition is prepared:

| | |
|---|---|
| Mixture of 80% cetyl/stearyl alcohol and 20% cetyl/stearyl alcohol oxyethylenated with 33 mol of ethyleneoxide | 7.5 g |
| Mixture of non-self-emulsifying glycerol mono- and distearates | 1.8 g |
| Cetyl alcohol | 1 g |
| Myristyl alcohol | 0.6 g |
| Sorbitol in 70% strength aqueous solution | 3 g |
| Isopropyl palmitate | 10 g |
| Liquid paraffin | 7 g |
| Extract of annatto in soybean oil assaying at approximately 3.8% of bixin (suspension in oil) | 0.22 g |
| 3-Benzylidene-dl-camphor | 1.5 g |
| 2-Hydroxy-4-(n-octyloxy)benzophenone (UVINUL 408) | 0.7 g |
| Preservative, perfume qs | |
| Water qs | 100 g |

EXAMPLE 4

A sun cream having the following composition is prepared:

| | |
|---|---|
| Lanolin | 7 g |
| Triester of glycerin and $C_{10-18}$ fatty acid | 5 g |
| Ester of polyethoxylated oleic acid and glycerol, sold by the company GATTEFOSSE under the name "LABRAFIL M 1969 CS" | 2.5 g |
| Mixture of glycerol stearate and stearate of polyethylene glycol (100 mol of ethyleneoxide) | 5 g |
| Polyphenylmethylsiloxane | 0.5 g |
| Stearyl alcohol | 1 g |
| Stearic acid | 2.5 g |
| Mixture of cetyl phosphate and diethanolamine/cetyl phosphate sold by the company GIVAUDAN under the name "AMPHISOL" | 0.5 g |
| Isopropyl myristate | 9 g |
| Extract of annatto in soybean oil, assaying at approximately 3.8% of bixin (suspension in oil) | 0.15 g |
| 3-(4'-Methylbenzylidene)-dl-camphor (EUSOLEX 6300) | 2 g |
| Triethanolamine | 0.2 g |
| Preservative, perfume qs | |
| Water qs | 100 g |

EXAMPLE 5

A sun oil having the following composition is prepared:

| | |
|---|---|
| N-(2-Ethylhexyl)-3-(3'-methoxy-4'-n-butoxybenzylidene)-10-camphorsulphonamide | 5 g |
| Extract of annatto in soybean oil assaying at approximately 0.12% of bixin (lipid-soluble extract) | 3 g |
| Sunflower oil | 25 g |
| Benzoate of $C_{12}-C_{15}$ alcohols, sold by the company FINETEX under the name "FINSOLV TN" | 15 g |
| Sesame oil qs | 100 g |

EXAMPLE 6

A sun cream having the following composition is prepared:

| | |
|---|---|
| N-(2-Ethylhexyl)-4-(3'-methylidenecamphor)benzenesulphonamide | 1.5 g |
| N-(2-Ethylhexyl)-3-benzylidene-10-camphorsulphonamide | 2.5 g |
| Extract of annatto in soybean oil assaying at approximately 0.12% of bixin (lipid-soluble extract) | 7.5 g |
| 50:50 Mixture of glycerol stearate and stearate of polyethylene glycol (100 mol of ethyleneoxide) | 8 g |
| Stearyl alcohol | 6 g |
| Benzoate of $C_{12}-C_{15}$ alcohols, sold by the company FINETEX under the name "FINSOLV TN" | 20 g |
| Glycerin | 5 g |
| Water qs | 100 g |

We claim:

1. In a light-stable cosmetic sunscreening composition for protecting the human epidermis against UV radiation which comprises bixin in a cosmetically-acceptable vehicle comprising at least one fatty phase, wherein the improvement comprising at least 1% by weight of one or more lipidsoluble UV radiation screening agents wherein said agent is selected from the group consisting of 3-benzylidene-dl-camphor; 3-(4-methylbenzylidene)-dl-camphor (EUSOLEX 6300); 3-benzylidenecamphors substituted at the para position, having the following formula:

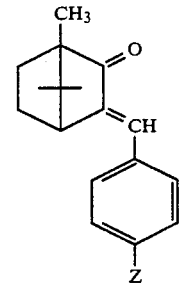

(I)

where Z denotes the groups $-CH_2I$, $-CH_2Br$ or $-CHBr_2$, $-CH_2R$, $-CHR'R'$, $-CHO$, $-COOR''$ in which:

R denotes $-NR_1R_2$, $-OR_4$, $-OCOR_5$, $-SR_6$, $-CN$, $-COOR''$, ($C_{1-4}$ alkyl)sulphinyl, $R_1$ and $R_2$ denote H, $C_1-C_{18}$ alkyl, $C_1-C_4$ hydroxyalkyl or alternatively form, together with the nitrogen atom, a heterocycle selected from the group consisting of morpholine, piperidine and piperazine, $R_4$ denotes H, $C_1$-$C_{18}$ alkyl, $C_1$-$C_4$ hydroxyalkyl, polyoxyethylene, aryl selected from the group consisting of, substituted phenyl, unsubstituted phenyl, substituted naphthyl, unsubstituted naphthyl, menthyl, and dialkylaminoalkyl in which the alkyl radicals contain from 1 to 4 carbon atoms, $R_5$ denotes $C_1$-$C_{18}$ alkyl, $C_2$-$C_{18}$ alkenyl, aryl selected from the group consisting substituted phenyl, unsubstituted phenyl, substituted naphthyl, unsubstituted naphthyl and 5- to 6-membered aromatic or nonaromatic heterocycle, $R_6$ denotes H, $C_1$=$C_4$ alkyl, $C_1$-$C_4$ aminoalkyl, $C_1$-$C_4$ hydroxyalkyl, aryl selected from the group consisting of substituted phenyl, unsubstituted phenyl, substituted naphthyl, unsubstituted naphthyl and benzothiazolyl, R' denoted $-OR'_4$ or $-SR'_6$, in which $R'_4$ and $R'_6$ can have, respectively, the same meanings as $R_4$ and $R_6$, except the meanings hydrogen, polyoxyethylene, hydroxyalkyl and aryl, $R''$ = $C_1$-$C_{18}$ alkyl or $C_2$-$C_{18}$ alkenyl;

sulphonamides derived from 3-benzylidenecamphor, having the formula:

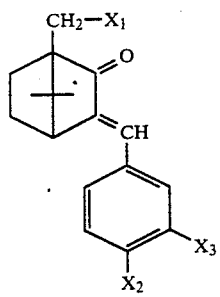

(II)

in which
$X_1$ denotes a hydrogen atom or a radical Y;
$X_2$ denotes a hydrogen or halogen atom, a $C_1$-$C_4$ alkyl or alkoxy radical or a radical Y or Z;
$X_3$ denotes a hydrogen or halogen atom, a $C_1$-$C_4$ alkyl or alkoxy radical or a radical Y or Z;
or alternatively $X_2$ and $X_3$ together form an alkylenedioxy group containing 1 or 2 carbon atoms;
Y denotes a radical

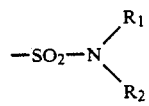

in which
$R_1$ denotes a hydrogen atom or a $C_1$-$C_4$ alkyl or hydroxyalkyl radical;
$R_2$ denotes a hydrogen atom, a linear or branched alkyl or alkenyl, cycloalkyl, aryl or aralkyl radical, these different radicals containing 1 to 20 carbon atoms and being capable of being substituted with one or more hydroxy, alkoxy or dialkylamino groups,
it not being possible for $R_1$ and $R_2$ simultaneously to denote a hydrogen atom;
Z denotes a group selected from the group consisting of $Z_1$, $Z_2$ and $Z_3$, wherein:
$Z_1$ denotes

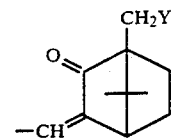

where Y has the meaning stated above,
$Z_2$ denotes

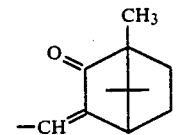

and
$Z_3$ denotes

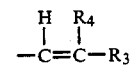

wherein $R_3$ denotes a hydrogen atom, a $-CN$ radical or a radical $-COR_5$;
$R_4$ denotes a radical $-COR_6$,
$R_5$ and $R_6$, which may be identical or different, being $C_1$-$C_{20}$ alkoxy or alkylamino groups;
with the proviso that one of the symbols $X_1$, $X_2$ and $X_3$ is different from the other two, and that
(a) where $X_1$ denotes a hydrogen atom,
$X_2$ and $X_3$ are different from one another and cannot assume the meanings $Z_2$ and $Z_3$, one of the two of necessity having the meaning Y or $Z_1$;
(b) where $X_1$ has the meaning Y
$X_2$ and $Z_3$ are different from Y and cannot simultaneously assume the meaning $Z_1$ or $Z_2$ or $Z_3$;
and a benzphenone selected from the group consisting of
2-hydroxy-4-methoxybenzophenone,
2-hydroxy-4-(n-octyloxy)benzophenone,
4-phenylbenzophenone,
2-ethylhexyl 2-(4-phenylbenzoyl)benzoate,
2-hydroxy-4-methoxy-4'-methylbenzophenone,
2,2'-dihydroxy-4,4'-dimethoxybenzophenone,
2,2',4,4'-tetrahydroxybenzophenone,
2,4-dihydroxybenzophenone, and
2,2'-dihydroxy-4-methoxybenzophenone,
the amount of bixin in said composition being at least 0.0025% by weight.

2. A composition according to claim 1, which contains 0.0025% to 0.06% by weight of bixin.

3. A composition according to claim 1, which contains 0.0025% to 0.009% by weight of bixin.

4. A composition according to claim 1 containing 1 to 20% by weight of said screening agent.

5. A composition according to claim 1 containing 2 to 10% by weight of said screening agent.

6. A composition according to claim 1, wherein bixin is used in the form of an oily extract of annatto containing at least 0.1% by weight of bixin.

7. A composition according to claim 1, wherein the oily extract of annatto is in the form of a lipid-soluble extract or of a suspension in an oil.

8. A composition according to claim 7, wherein the oily extract of annatto contains oils selected from the group consisting of soybean oil, pequia oil, sweet almond oil, coffee oil and sunflower oil.

9. A composition according to claim 1, which contains one or more lipid-soluble UV radiation screening agents of formula (II), selected from the group consisting of:

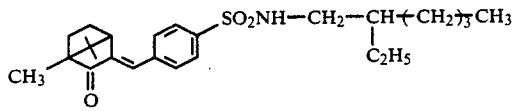

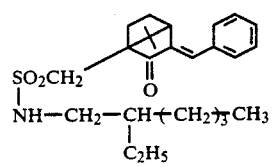

and

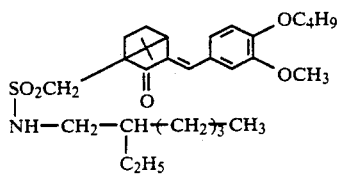

10. A composition according to claim 1, wherein the lipid-soluble UV radiation screening agent is 3-benzylidene-dl-camphor.

11. A composition according to claim 1, which contains 2-hydroxy-4-methoxy-benzophenone.

12. A composition according to claim 1, which comprises other water-soluble or lipid-soluble UV-A or UV-B filters.

13. A composition according to claim 1 in the form of an oily or oleoalcoholic lotion, a fatty or oleoalcoholic gel, a solid stick, an emulsion, or an aerosol.

14. A composition according to claim 1, which contains, in addition cosmetic adjuvants selected from the group consisting of thickeners, emollients, moisturizers, surfactants, preservatives, antifoams, perfumes, oils, waxes, lower polyols, propellants, colourings, vitamins and opacifiers.

15. A composition according to claim 1 in the form of an emulsion comprising a cosmetic vehicle selected from the group consisting of fatty alcohols, fatty acid esters, fatty triglycerides, fatty acids, lanolin, natural waxes, synthetic waxes, and oils, emulsifiers and water.

16. A composition according to claim 1 in the form of an oily lotion comprising a cosmetic vehicle selected from the group consisting of fatty acid esters, natural waxes, synthetic waxes and oils.

17. Process for protecting the human epidermis against UV radiation, which consists in applying on the skin an effective quantity of a light-stable cosmetic sunscreening composition as defined in claim 1.

* * * * *